United States Patent [19]
Eskelä

[11] Patent Number: 5,365,938
[45] Date of Patent: Nov. 22, 1994

[54] APPARATUS FOR SEPARATING A LIQUID COMPONENT FROM EXHALATION AIR TO BE DELIVERED TO AN ANALYZING UNIT

[75] Inventor: Esa Eskelä, Espoo, Finland

[73] Assignee: Instrumentarium Corporation, Finland

[21] Appl. No.: 195,575

[22] Filed: Feb. 14, 1994

Related U.S. Application Data

[63] Continuation of Ser. No. 990,601, Dec. 14, 1992, abandoned.

[30] Foreign Application Priority Data

Dec. 20, 1991 [FI] Finland ................................. 916041

[51] Int. Cl.$^5$ ............................................. A61B 5/097
[52] U.S. Cl. ............................................. 128/719; 96/6
[58] Field of Search ........ 128/716, 719, 725, 729–730; 73/863.23; 55/158, 270, 274, 350

[56] References Cited

U.S. PATENT DOCUMENTS

| | | |
|---|---|---|
| 4,304,578 | 12/1981 | Hakala et al. |
| 4,382,806 | 5/1983 | Hakala et al. |
| 4,558,708 | 12/1985 | Labuda et al. ............ 128/719 |
| 4,679,573 | 7/1987 | Parnoff et al. ............ 128/716 |
| 4,798,676 | 1/1989 | Matkovich |
| 4,886,528 | 12/1989 | Aaltonen et al. |

FOREIGN PATENT DOCUMENTS 2053022 2/1982 United Kingdom.
8103266 11/1981 WIPO.

Primary Examiner—Angela D. Sykes
Attorney, Agent, or Firm—Andrus, Sceales, Starke & Sawall

[57] ABSTRACT

An apparatus (1) for separating a liquid component from the exhalation gas of a patient to be delivered to one or more analyzing units (3, 4). The apparatus comprises a first chamber (10) for receiving therein an exhalation gas coming from a patient and in which the inflowing gas divides into two components in a manner that some of the gas flows to an analyzing unit and some of the gas, as well as a liquid component possibly entrapped in the exhalation gas, is conducted out past the analyzing unit, a second chamber (12), through which a patient's exhalation gas flows from the first chamber to an analyzing unit, and a gas-permeable wall (11), which separates these chambers and through which the gas flows from the first chamber into the second chamber. Upstream of the wall (11) there is a filter (20), the exhalation gas of a patient flowing through this filter prior penetrating through the wall (11) and the filter (20) allowing therethrough the flow of a liquid component possibly entrapped in the gas.

24 Claims, 2 Drawing Sheets

A-A

B-B

C-C

APPARATUS FOR SEPARATING A LIQUID COMPONENT FROM EXHALATION AIR TO BE DELIVERED TO AN ANALYZING UNIT

The present application is a continuation application of U.S. patent application, Ser. No. 07/990,601, filed Dec. 14, 1992, and now abandoned.

The present invention relates to an apparatus for separating a liquid component from a patient's exhalation gas to be delivered to one or more analyzing units, said apparatus comprising a first chamber, wherein the exhalation gas coming from a patient is delivered and wherein the inflowing gas is divided into two components in a manner that some of the gas flows to an analyzing unit and some of the gas, as well as a liquid component possibly entrapped in the exhalation gas, is carried away past the analyzing unit, a second chamber, through which a patient's exhalation gas flows from the first chamber to the analyzing unit, and a gas permeable wall, which separates these chambers and through which the gas flows from first chamber to second chamber.

BACKGROUND OF THE INVENTION—FIELD OF THE INVENTION

In anesthesia or in intensive care, the condition of a patient is often monitored e.g. by analyzing the air exhaled by a patient. Special attention is paid to the carbon dioxide content exhaled by a patient. The content of anesthetic gases is also often monitored. Therefore, a small portion of the exhalation air is delivered to a analyzing unit. This sample often carries along to the analyzing unit some water vapour, which condenses into droplets, and also some dust, mucus and blood. Such components carried along with the sample have a detrimental effect on the analyzing unit and measuring result. This is why the liquid components are often removed and collected from a gas sample upstream of the actual analyzing unit. A water separator and a method developed for this purpose are disclosed in U.S. Pat. Nos. 4,304,578 and 4,382,806. In order to separate liquid components, a gas sample is delivered into a rather small chamber, wherein the flow divides into two components.

The main flow keeps running from the top section of this chamber to an analyzing unit while the minor side flow is carried from the bottom section of the chamber out of reach of the analyzing unit, usually by way of a water receiver. The purpose is to condense the liquid, definitely vapourized by this time, condensate on the chamber walls and to carry on its passage down to a water receiver together with the rest of the liquid secretion. However these solutions are not totally sufficient, since some of the liquid components may still find access to an analyzing unit along with the main flow.

According to later solution described in U.S. Pat. No. 4,886,528 a chamber, wherein a liquid component is separated from a gas flow, is divided into two sections by means of a gas permeable and liquid-impermeable material. Thus, a sample picked up from the exhalation air of a patient is delivered into the first chamber of a water separator, from which the liquid component along with a minor amount of gas is sucked away, usually by way of a water receiver. Most of the gas flow received in the first chamber is sucked through the liquid-impermeable material into the second chamber and further to an analyzing unit. This material prevents effectively the passage of liquid to the analyzing unit.

The last described solution works well as long as just a moderate amount of liquid secretions are entrapped in the exhalation air of a patient. If, for some reason, however, a patient secretes e.g. mucus more than in a normal case, the liquid-impermeable material installed in the chamber will be choked up rather quickly, thus preventing the passage of gas samples to the analyzing unit.

SUMMARY OF THE PRESENT INVENTION

An object of this invention is to overcome the above problems. Thus, the object is to provide an apparatus for removing a gas-entrapped liquid component from a gas to be delivered to the analyzing unit of a gas analyzer. Another object is to provide an apparatus for removing a solid component entrapped in the exhalation air of a patient from an exhalation gas to be delivered to the analyzing unit of a gas analyzer. A particular object is to provide an apparatus, which is suitable for removing a liquid or solid component entrapped in an exhalation gas to be delivered to the analyzing unit of a gas analyzer and which has a long service life even when used for examining the exhalation gas of a patient producing plenty of secretions. Most particularly, an object is to provide an apparatus, which is suitable for removing a liquid or solid component entrapped in an exhalation gas to be delivered to the analyzing unit of a gas analyzer and which is capable of substantially reducing the choking possibility of a gas-permeable and liquid-impermeable filter used therein.

The characterizing features of the invention are disclosed in the appended claims.

The basic concept in the invention is that the exhalation gas of a patient, flowing towards an analyzing unit and carrying along some secretion, usually in liquid or solid state, is passed through a filter prior to its arrival in the analyzing unit for analysis. The filter is preferably made of a fibrous material. Downstream of the filter there is a gas-permeable wall, which is preferably also impervious to liquid. Both the filter and the wall can be arranged side by side, preferably in contact with each other. Some of the flow, which does not pass through the hydrophobic wall, is branched away e.g. by means of a receiver vessel. A liquid component affecting the gas flows is also removed into the receiver along with this side flow. On the other hand, a gas flow after passing through the filter and the wall proceeds on to the analyzing unit.

A fibrous material used in the filter does not detrimentally interfere with the flow of either a liquid or a gaseous component. In a preferred case, however, this filter binds solid components, such as dust particles, entrapped in the exhalation gas. This is desirable since the dust accumulated on the gas-permeable and liquid-impermeable wall expands upon wetting, whereby this hydrophobic wall is gradually choked up. In order to bring a solid component entrapped in the exhalation air to adhere to the filter of a fibrous material, it is referred to have the filter material electrically charged.

The fibers for composing a filter should be sufficiently large in size since, the larger the fibers against the surface of a wall the more wall surface will be uncovered for the gas to pass through. Preferably, the fiber should have a mean diameter of at least 50 $\mu$m. This type of filter, which is in contact with a hydrophobic wall, prevents the development of a fluid film on the wall surface. The fiber also creates a sort of outlet passage for the liquid accumulated on the wall, especially when the wall is located above the fiber. Thus, the fiber serves to cleanse the wall. A fluid film covering the entire surface prevents the passage of a gas flow to the analyzing unit.

Preferably, the material used in the filter should not substantially absorb liquid, so that moisture in the gas-flowing duct does not increase. As a result of moisture a water-absorbing filter would expand and this might cause blocking of the flow duct. A suitable fiber material is e.g. polymer, a good example being polypropylene.

BRIEF DESCRIPTION OF THE DRAWING

The invention will now be described in more detail with reference made to the accompanying patent drawings, in which.

DETAILED DESCRIPTION OF THE PREFERRED EMBODIMENTS

Figure 1:
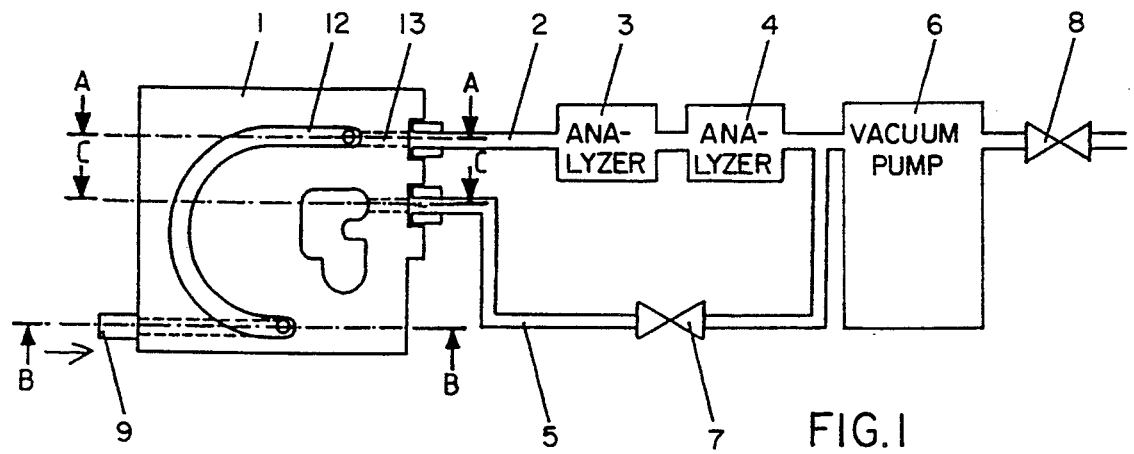
FIG. 1 shows an apparatus according to a preferred embodiment, suitable for separating a liquid component and coupled to a gas analyzer shown in a schematic view.

As shown in FIG. 1, a sample coming from the respiratory tracts of a patient is delivered to an apparatus 1 for separating a liquid component from a gaseous component. A liquid entrapped in the respiration of a patient is separated from a gas prior to conducting the gas sample along a line 2 to one or more analyzing units 3 and/or 4 for analysis. The analyzing unit can effect e.g. the identification or content measurement of one or several gases. In the exemplary case shown in the figure, the analyzing unit 3 measures the content of carbon dioxide, nitrous oxide and anesthetic gas while the analyzing unit 4 effects the identification of one or more components contained in the gas.

Some of the flow received in apparatus 1 is directed past analyzing unit 3 or 4 along a line 5. Preferably, the flow by-passing the analyzing unit is lesser than the one passing through it. The flow to apparatus 1 and further along lines 2 and 5 occurs through the action of vacuum, which is created by means of a pump 6. In order to control the flow running along line 5, this line is fitted with a flow-restricting element 7 upstream of pump 6. Thus, this element can be used for adjusting the mutual relationship between flows occurring through lines 2 and 5. Furthermore, downstream of pump 6 there is another flow-restricting element 8 for adjusting the total flow occurring through the pump.

Figure 2:
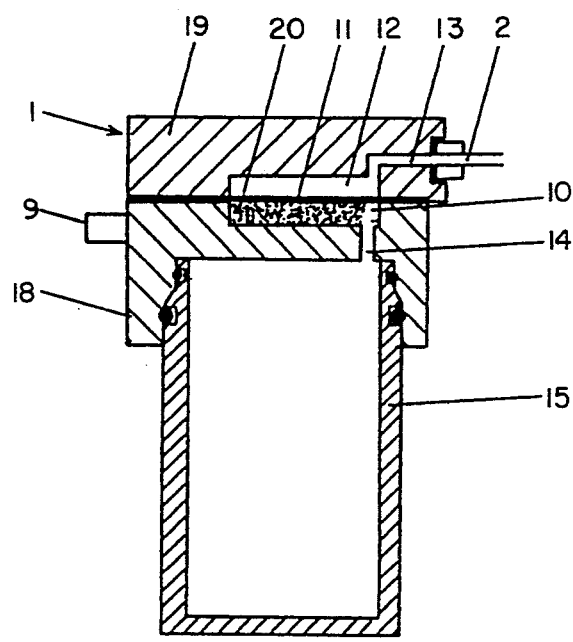
FIG. 2 shows the apparatus of FIG. 1 along a section A/A.
Figure 3:
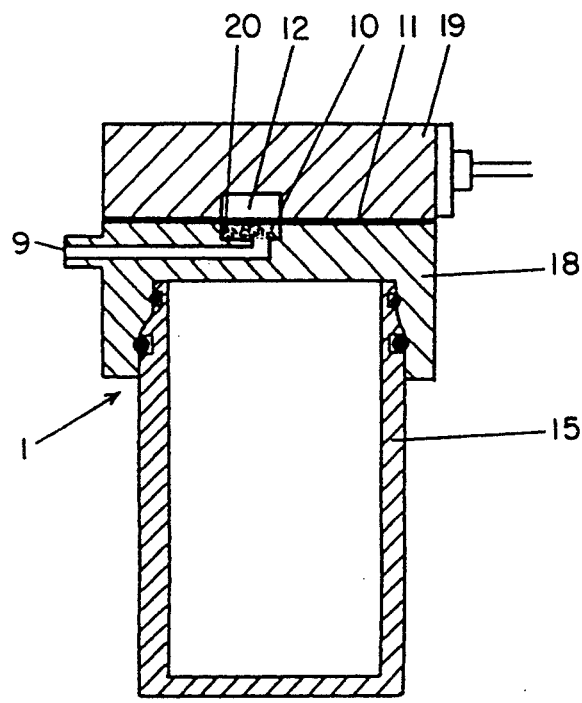
FIG. 3 shows the apparatus of FIG. 1 along a section B/B.
Figure 4:
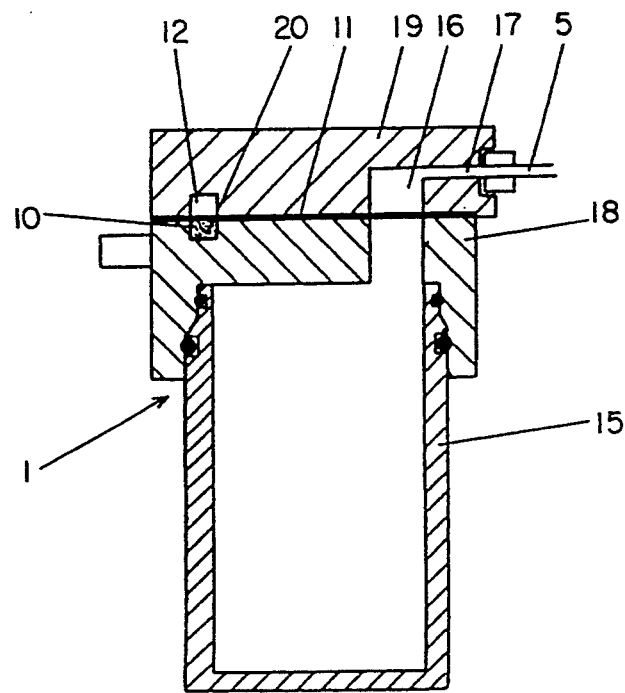
FIG. 4 shows the apparatus of FIG. 1 along a section C/C.

The exhalation gas of a patient arriving in apparatus 1 suitable for the separation of a liquid component is delivered, as shown in FIG. 3, along a tube 9 into a first chamber 10 confined at least partially by a wall 11. The wall 11 shown in FIGS. 2, 3 and 4 is preferably only permeable to gas. Thus, a liquid component or a solid component is not able penetrate therethrough but is filtered out. On the other side of this wall is a second chamber 12 for receiving a gas from first chamber 10 and through porous wall 11. From chamber 12 the gas flows along a tube 13 into line 2 leading to analyzing unit 3.

The liquid component received in first chamber 10 carries on along a tube 14 preferably into a receiver 15, as shown in FIG. 2. Also some of the gas received in chamber 10 flows away therefrom by way of the receiver along tube 5.

Particularly in FIG. 4 there is shown a preferred solution for preventing the passage of a liquid held in the receiver to pump 6. According to this, the gas escapes from the top receiver end into a third chamber 16 through a porous wall 11 identical to that between first and second chambers 10 and 12. There is a connection by way of a tube 17 from chamber 16 to line 5 leading to pump 6.

In the preferred embodiments shown in the figures, said first and second chambers 10 and 12 are elongated and tubular and provided between two opposite blocks 18 and 19. According to this preferred embodiment, said porous wall 11 is provided between these two blocks. In order to achieve easy draining, said receiver 15 is removable from blocks 18 and 19 enclosing the chambers.

According to the present invention, upstream of a porous wall 11, which prevents the further passage of a liquid component along with a gaseous component for analysis, the flow coming from a patient is directed through a fibrous filter 20. The best location for a filter is in first chamber 10, the flow escaping there from being divided into two components as described above. Furthermore, in order to achieve the best possible result, said filter 20 should be located in a manner that the flow coming from a patient passes therethrough prior to branching the flow to an analyzing unit and past an analyzing unit. In a preferred case, a wall 11 and a filter 20 are adjacent to each other. According to the most preferred embodiment, a porous wall 11 and a fibrous filter 20 should be in contact with each other. Thus, a fibrous filter would cover at least a portion of the porous wall facing chamber 10. A good result is obtained when a filter covers at least such a portion of the porous wall that the flow of a gas to be delivered to an analyzing unit through this wall remains sufficient. For this reason, it is not necessary to use a filter to cover the entire porous wall 11 of a long chamber 10 shown in the figures but, instead, a smaller area will be sufficient. However, it is also possible to protect the entire porous wall with a filter. A preferred solution is to use a filter filling the cross-section of a chamber since, in that case, the flow progresses smoothly and there will be no opening for some of the flow to proceed at a faster rate than the flow penetrating through the filter. A filter material appropriate for this purpose is manufactured by the U.S. company 3M Company of St. Paul, Minn. under the tradename "Filtrete".

The use of a fibrous filter prevents effectively the blocking of porous wall 11. Particularly, if the exhalation air of a patient carries along a lot of mucus, the wall tends to block quite rapidly without a filter. Considering the tendency of a porous wall to block, the best system is such that a filter 20 is located below said porous wall 11.

Thus, a fibrous filter allows the flow of both a gas and a liquid therethrough. In a preferred case, the filter should not absorb liquid in itself but, instead, would allow all of it to flow therethrough into a receiver.

In order to obtain such a filter 20 that would prevent the passage of solid particles onto wall 11, it would be beneficial to use a material which is electrically charged. Hence, the particles adhere to the fiber through the action of electrical attraction and the porous wall remains clear.

The invention is by no means limited to the above embodiments but different details of the invention can be varied within the scope of the annexed claims.

I claim:

1. An apparatus for separating out a liquid entrained in the exhalation gas of a patient and for delivering the exhalation gas to at least one analyzing unit, said apparatus comprising:
first chamber means (10) for receiving exhalation gas from the patient;
second chamber means (12) downstream of said first chamber means in a gas flow path through said apparatus, said second chamber means delivering exhalation gas from said apparatus to the analyzing unit;
a gas-permeable, liquid-impermeable wall (11) separating said first and second chamber means and through which exhalation gas passes from said first chamber means to said second chamber means;
means for dividing the exhalation gas received in said first chamber means into a first portion which is discharged from said first chamber means and a second portion which passes through said gas-permeable wall; and
a filter (20) upstream of said wall along the gas flow path of said apparatus through which liquid material entrained in the gas flows, said filter separating said entrained liquid material from the exhalation gas and discharging said entrained liquid material from said first chamber means with said first gas portion.

2. An apparatus as set forth in claim 1, characterized in that said filter (20) is comprises of a fibrous material.

3. An apparatus as set forth in claim 2 characterized in that said filter (20) has a mean fiber diameter of at least 50 μm.

4. An apparatus as set forth in claim 2, characterized in that said filter (20) is located adjacent to the gas-permeable, liquid-impermeable wall (11).

5. An apparatus as set forth in claim 4, characterized in that said filter (20) and said gas-permeable, liquid-impermeable wall (11) are in contact with each other.

6. An apparatus as set forth in claim 1 characterized in that said filter allows both said first portion of the gas and the second portion of the gas to flow therethrough.

7. An apparatus as set forth in claim 1, characterized in that said filter (20) is located adjacent to the gas-permeable, liquid-impermeable wall (11).

8. An apparatus as set forth in claim 7, characterized in that said filter (20) and said gas-permeable, liquid-impermeable wall (11) are in contact with each other.

9. An apparatus as set forth in claim 1, characterized in that said filter (20) is located in the first chamber means (10).

10. An apparatus as set forth in claim 9, characterized in that said filter (20) fills the first chamber means (10) in a cross-sectional direction of said first chamber means.

11. An apparatus as set forth in claim 9, characterized in that said filter (20) fills the first chamber means (10) entirely.

12. An apparatus as set forth in claim 1, characterized in that the filter covers at least partially a surface of said gas-permeable, liquid-impermeable wall (11) facing said first chamber means (10).

13. An apparatus as set forth in claim 12, characterized in that a surface of said gas-impermeable, liquid-impermeable wall faces said first chamber means and the filter covers that portion of the surface of said gas-permeable wall (11) facing said first chamber means (10) that enables a sufficient amount of said second gas portion to be passed through said gas-permeable, liquid-impermeable wall.

14. An apparatus as set forth in claim 1, characterized in that an filter covers the entire surface of said wall (11), which faces said first chamber means (10).

15. An apparatus as set forth in claim 1, characterized in that said filter (20) is electrically charged.

16. An apparatus as set forth in claim 1, characterized in that the filter (20) is formed of a material that does not substantially absorb liquid.

17. An apparatus as set forth in claim 1, characterized in that the material forming the filter contains a polymer.

18. An apparatus as set forth in claim 17, characterized in that the material forming the filter comprises polypropylene material.

19. An apparatus as set forth in claim 1, characterized in that said wall (11) comprises a porous material, which is substantially impermeable to a liquid component but permeable to gas.

20. An apparatus as set forth in claim 1 further including receiving means coupled to said first chamber means for receiving the first portion of the gas.

21. The apparatus according to claim 20 wherein said receiving means includes a gas-permeable, liquid-impermeable wall through which said first portion of said gas passes for discharge from said receiving means.

22. An apparatus as set forth in claim 1 further defined as including at least one said analyzing unit coupled to said second chamber means to form patient monitoring apparatus.

23. Apparatus for separating an entrained liquid component from a gas comprising:
first chamber means for receiving the gas having the liquid component entrained therein;
second chamber means (12) downstream of said first chamber means in a gas flow path through said apparatus, said second chamber means delivered gas with the liquid component separated therefrom;
a gas-permeable, liquid-impermeable wall (11) separating said first and second chamber means and through which gas passes from said first chamber means to said second chamber means;
means for dividing the gas received in said first chamber means into a first portion which is discharged from said first chamber means and a second portion which passes through said wall, said dividing means including means (6) for applying a vacuum to said first and second chamber means;
a filter (20) upstream of said wall along the gas flow path of said apparatus through which liquid material entrained in the gas flows, said filter separating said entrained liquid material from the gas; and
receiving means (15) coupled to said first chamber means for receiving the first portion of the gas discharged from said first chamber means and said entrained liquid material.

24. The apparatus according to claim 23 wherein said receiving means includes a gas-permeable, liquid-impermeable wall through which said first portion of said gas passes for discharge from said receiving means.

* * * * *

UNITED STATES PATENT AND TRADEMARK OFFICE
CERTIFICATE OF CORRECTION

PATENT NO. : 5,365,938
DATED : November 22, 1994
INVENTOR(S) : Eskelä

It is certified that error appears in the above-indentified patent and that said Letters Patent is hereby corrected as shown below:

CLAIM 2, Col. 5, Line 37, delete "comprises" and substitute therefor ---comprised---; CLAIM 13, Col. 6, Line 2, delete "gas-impermeable" substitute therefor ---gas-permeable---; CLAIM 13, Col. 6, Line 5, after "permeable" insert ---, liquid-impermeable---; CLAIM 14, Col. 6, Line 10, delete "an" and substitute therefor ---the---; CLAIM 14, Col. 6, Line 10, delete "the" and substitute therefor ---an---; CLAIM 23, Col. 6, Line 43, delete "delivered" and substitute therefor ---delivering---

Signed and Sealed this

Ninth Day of May, 1995

Attest:

BRUCE LEHMAN

Attesting Officer

Commissioner of Patents and Trademarks